United States Patent [19]

Long

[11] Patent Number: 5,658,273
[45] Date of Patent: Aug. 19, 1997

[54] APPARATUS AND METHOD FOR SUPPORTING AND CLEANING AN ELONGATE LAPAROSCOPIC SURGICAL TOOL USED VIA A CANNULA

[75] Inventor: Gary Long, Cincinnati, Ohio

[73] Assignee: Laser Centers of America, Cincinnati, Ohio

[21] Appl. No.: 505,544

[22] Filed: Jul. 21, 1995

[51] Int. Cl.⁶ .................................................. A61B 17/36
[52] U.S. Cl. .................................................. 606/1; 606/15
[58] Field of Search ............................. 606/14, 15, 16, 606/17, 10, 11, 12, 1

[56] References Cited

U.S. PATENT DOCUMENTS

| | | | |
|---|---|---|---|
| 5,156,604 | 10/1992 | Hessel et al. | 606/15 |
| 5,164,945 | 11/1992 | Long et al. | |
| 5,240,675 | 8/1993 | Wilk et al. | 606/15 |
| 5,275,596 | 1/1994 | Long et al. | |
| 5,276,693 | 1/1994 | Long et al. | |
| 5,306,274 | 4/1994 | Long | |
| 5,320,617 | 6/1994 | Leach | 606/15 |
| 5,320,620 | 6/1994 | Long et al. | |
| 5,342,355 | 8/1994 | Long | |
| 5,456,681 | 10/1995 | Hajjar | 606/15 |

Primary Examiner—Lee S. Cohen
Assistant Examiner—Sonya Harris-Ogugua
Attorney, Agent, or Firm—Lowe, Price, LeBlanc & Becker

[57] ABSTRACT

An apparatus and a method are provided in which a cylindrical body is shaped and sized to sealingly and closely fit into a conventional cannula. An elongate surgical instrument is inserted into the cylindrical body through a resilient seal so as to extend past and be in pressing contact with distal ends of a plurality of bristles supported to the cylindrical body inside a distal end thereof. The sealing element and the bristles cooperate to support the surgical instrument substantially axially of the cylindrical body and the cannula within which it is contained. Relative motion of the surgical instrument causes a rubbing action of the bristles contacting its outer surface and this serves to remove any incidental surgical debris, e.g., excised tissue, coagulated fluids, and the like, from the bristle-contacted outer surface of the surgical instrument both when it is moved during use and when it is removed from the cylindrical body.

19 Claims, 3 Drawing Sheets

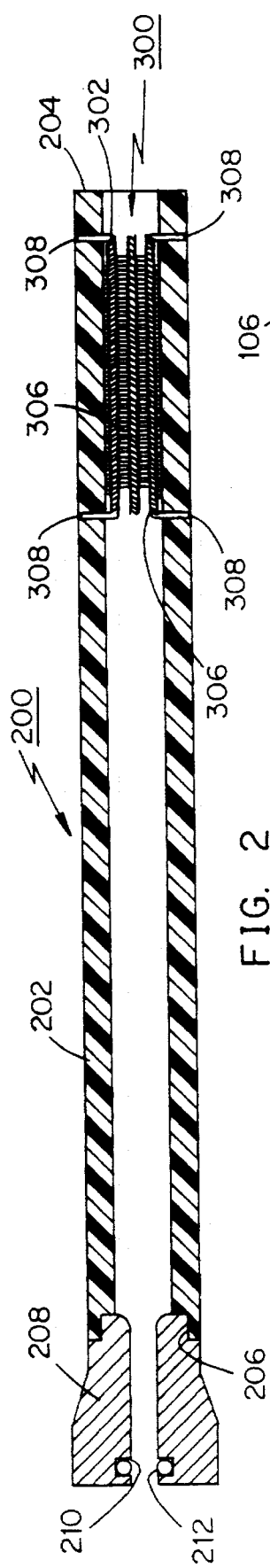
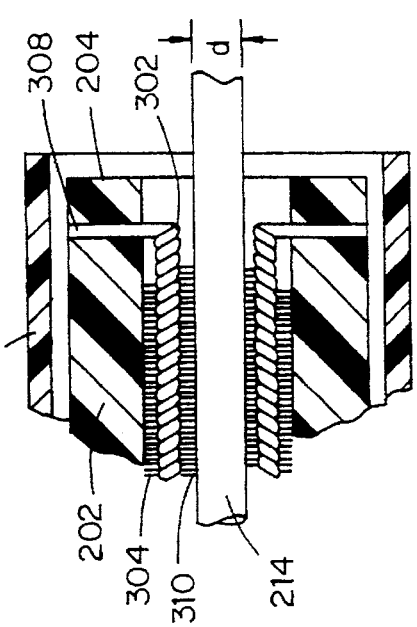
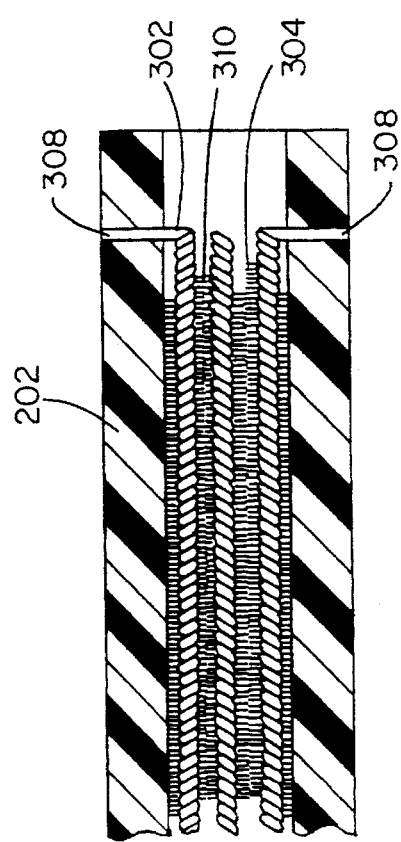
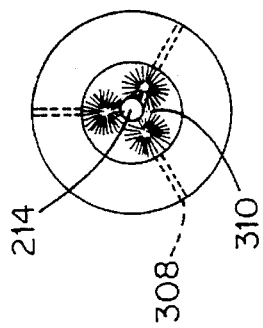
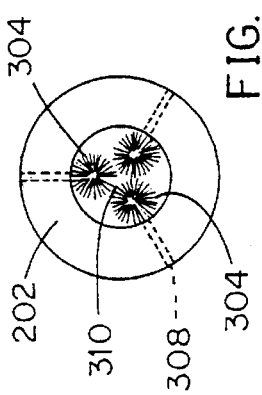
FIG. 2
FIG. 4
FIG. 3
FIG. 5(A)
FIG. 5(B)

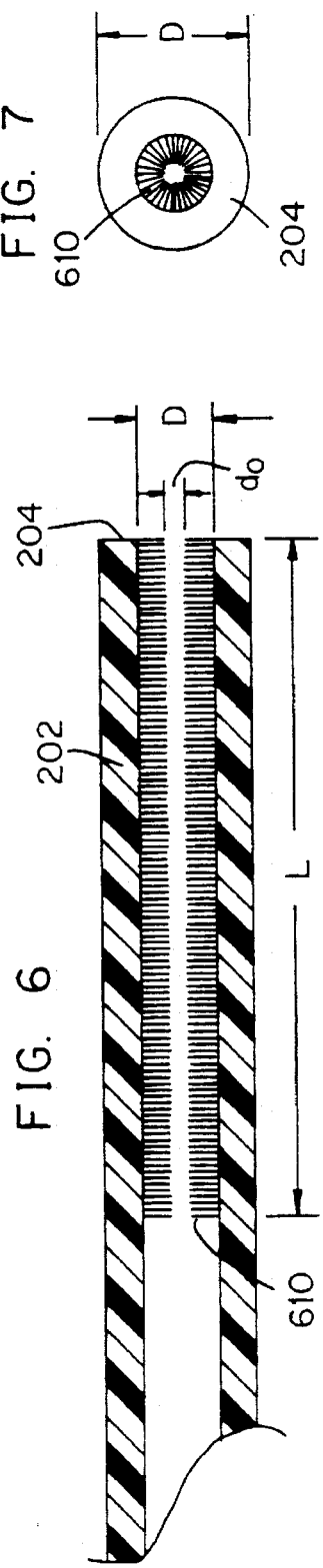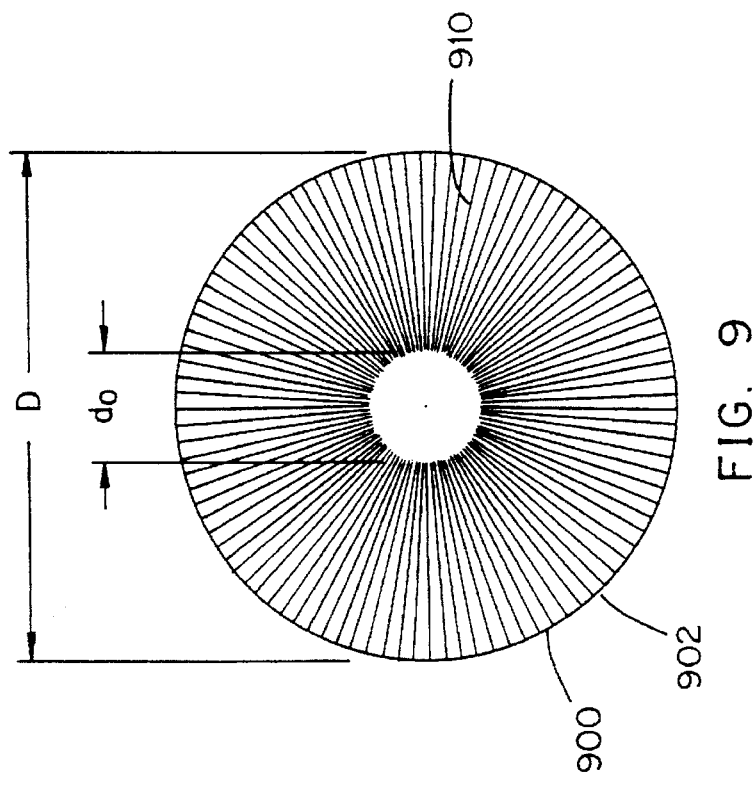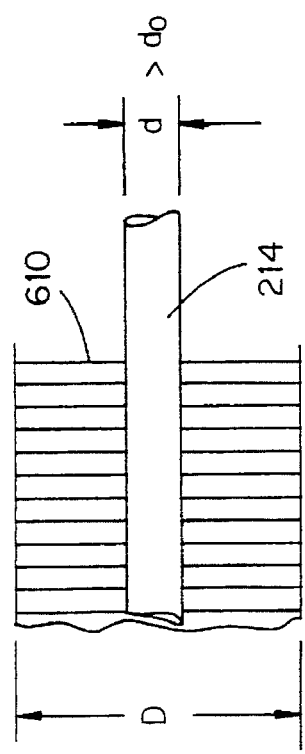

APPARATUS AND METHOD FOR SUPPORTING AND CLEANING AN ELONGATE LAPAROSCOPIC SURGICAL TOOL USED VIA A CANNULA

FIELD OF THE INVENTION

This invention relates to an apparatus and a method for rotatably and slidably supporting an elongate surgical tool inside a conventional cannula during laparoscopic surgery, and more particularly to an apparatus and a method for rotatably and slidably supporting a laparoscopic surgical tool (such as a laser-powered instrument for incising, coagulating and cauterizing tissue) centrally of a conventional cannula while ensuring that any material from a surgical site which attaches to the outer surface of the distal end portion of the surgical tool is removed therefrom as the surgical tool is moved during its use and removal from the cannula.

BACKGROUND OF THE RELATED ART

Numerous elongate surgical tools are now available to enable a surgeon to operate deep inside human bodies to make intricate incisions, e.g., to separate cancerous tissue, without having to make major cuts from the outside into the patient's body. A prime example of the use of such tools is to be found in laparoscopic surgery in which the surgeon typically employs one or more cannulae through which to insert elongate tools to provide lighting and viewing of a surgical site, to provide lavage, to provide insufflation with carbon dioxide to permit access to the surgical site, and to apply the distal working ends of a variety of surgical tools.

These tools are shaped, formed and operable to precisely cut tissue, to cauterize incised vessels from which body fluids may leak at and around the surgical site, and to locally coagulate blood as appropriate. Numerous such surgical tools are known and more are being invented all the time. Some of the tools apply mechanical force to one or more sharp edges to cut tissue or to grab and/or manipulate tissue, while others employ carefully focused laser beams to cause very rapid heating and destruction of target tissue. Yet other tools allow the local application of controlled high frequency current to obtain comparable results and/or to coagulate body fluids or to cauterize cut vessels.

Examples of recently developed surgical tools and instruments of pertinent type, which have slim elongate cylindrical bodies and which are powered by laser energy or electricity to deliver controlled amounts of energy to tissues for various surgical procedures, include those described in U.S. Pat. Nos. 5,164,945, 5,275,596, 5,276,693, 5,306,274, 5,320,620, and 5,342,355, relevant portions whereof are incorporated herein by reference.

The type of surgery discussed above almost inevitably causes small elements of incised tissue, coagulated fluids, and charred material to adhere to the outside surfaces of the surgical tool. As the surgeon moves the tool in translation within the surrounding cannula, or turns the tool to apply it at different angles, the incidental debris which attaches to the outside of the surgical tool can pose difficulties. It is not always possible to remove such material by suction and lavage. Furthermore, the surgeon may wish to insert different tools through the same cannula to perform different surgical functions or to extract tissue samples for prompt testing thereof, and may need to use the same tool intermittently in conjunction with other tools.

In conducting the large variety of surgical activities discussed above, it would be very helpful to the surgeon if means were provided which would ensure that tissue debris is very easily and continuously removed from the outside surface of the distal or working end of the surgical tool while the surgical tool is slidably and rotatably supported within the cannula. It is also desirable that the surgeon be able to remove a first tool, utilize a second tool through the same cannula, and reinsert the first tool back into the cannula without having tissue debris interfering with the activity or inhibiting the surgical procedure in any significant manner.

It is believed that no such devices are presently available, and the present invention is expressly designed to meet this long-felt need. The simplicity and functional advantages of the present invention will be best understood with reference to the drawing figures and detailed description provided hereinbelow.

SUMMARY OF THE INVENTION

It is a principal object of this invention to provide an apparatus which can be used with a conventional cylindrical cannula to support an elongate surgical instrument employed therethrough and to ensure that any incidental tissue or surgical debris which may tend to attach or adhere to the outer surface of the surgical instrument is removed therefrom as the instrument is used and also when it is removed from the cannula.

Another object of this invention is to provide an apparatus usable in conjunction with a conventional cylindrical cannula of the type typically used for laparoscopic surgical procedures so as to support and clean during use an elongate surgical instrument inserted into the cannula.

In another aspect of this invention, there is provided a method by which an elongate surgical instrument may be supported for translational and rotational motion inside a conventional cannula in such a manner that incidental surgical debris and tissue which would otherwise adhere to an outer surface of the surgical instrument is scraped off as the instrument is used and also when the instrument is extracted from the cannula.

These and other related objects are realized by providing an apparatus for supporting and cleaning an elongate surgical instrument during use thereof within a cylindrical cannula, which apparatus has a cylindrical body shaped and sized to seal to and fit closely inside the cannula along a longitudinal axis thereof. A plurality of bristles is mounted inside a distal end of the cylindrical body. A portion of the bristles are so disposed as to be directed generally radially inward of the cylindrical body. The cylindrical body, at a proximal end, has a cylindrical inlet element fitted to hold a sealing element for resiliently sealing around an outer surface of an elongate surgical instrument inserted therethrough into the cannula. The bristles which are oriented generally radially inward of the cylindrical body are sized to contact an outer surface of a cylindrical end of the surgical instrument. This structure ensures support and cleaning of the elongate surgical instrument during use thereof.

In another aspect of this invention, there is provided a method for supporting and cleaning an elongate surgical instrument during use thereof within a conventional cylindrical cannula. The method includes the steps of sealing to and closely fitting into and along a longitudinal axis of the cannula a correspondingly shaped and sized cylindrical body and providing inside a distal end of the cylindrical body a plurality of bristles a portion of which are disposed to be directed generally radially inward of the cylindrical body. A sealing element is provided at a proximal end of the cylindrical body, and is shaped, sized and disposed to resiliently fit sealingly around an outer surface of an elongate surgical instrument inserted therethrough. A distal end portion of the surgical instrument is disposed during use so as to be contacted by the generally radially inwardly disposed portion of the bristles. The sealing element and the bristles thus cooperatively contact the outer surface of the surgical instrument and seal and support it within the cannula in a movable manner during a surgical operation. Relative movement between the surgical instrument and the contacting fibers results in scraping off of any surgical debris which would otherwise adhere to the outside surface of the surgical instrument.

Details of the invented apparatus and the associated method will be understood from the following description thereof, with reference to the drawing figures. Persons of ordinary skill in the art are expected to consider obvious modifications of the disclosed invention, and such modifications and variations are intended to be comprehended within the disclosed invention.

DETAILED DESCRIPTION OF THE DRAWING

FIG. 2 is a longitudinal cross-sectional view of a device according to a first preferred embodiment of this invention.

FIG. 3 is an enlarged longitudinal cross-sectional view of certain principal elements according to the first preferred embodiment of this invention.

FIG. 4 is an even more enlarged view of the extreme distal end of the first preferred embodiment of this invention, to clarify certain dimensional relationships and the manner of operation according to the first preferred embodiment.

Figure 1:
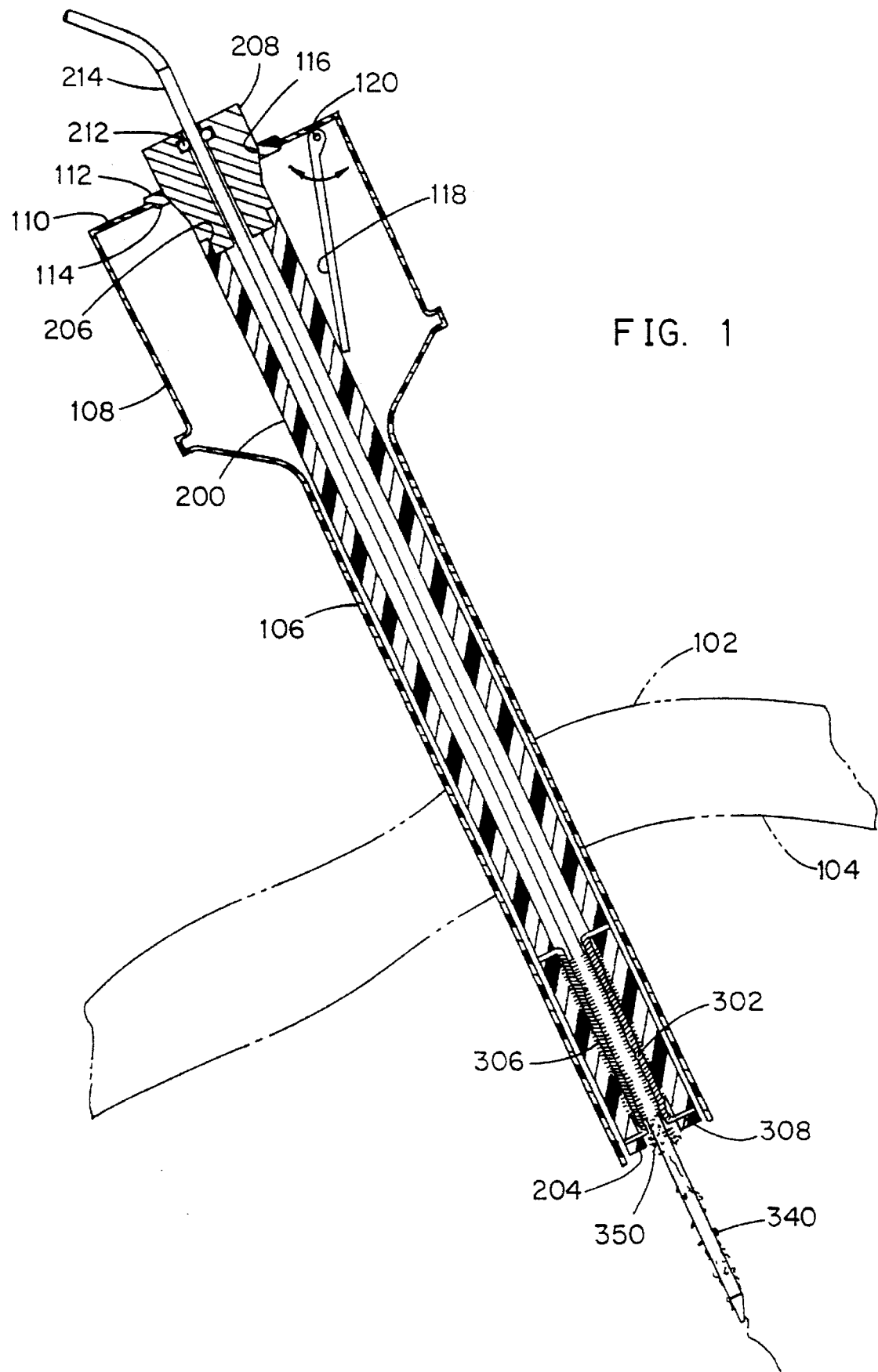
FIG. 1 is a longitudinal cross-sectional view of a cannula with the structure according to this invention deployed therein as it should be in the course of performing a laparoscopic surgical procedure.

FIG. 5(A) and 5(B) are respective distal end views of the first preferred embodiment of the invention, respectively with and without a surgical tool disposed within.

FIG. 6 is a longitudinal cross-sectional view of the device according to a second preferred embodiment of the invention.

FIG. 7 is distal end view of the second preferred embodiment according to FIG. 6.

FIG. 8 is an enlarged view of a portion of key elements of the second preferred embodiment schematically showing a portion of an elongate surgical tool in place, to explain certain dimensional relationships.

FIG. 9 is an enlarged distal end view of a portion of the structure per FIG. 7, to explain certain dimensional relationships.

DETAILED DESCRIPTION OF THE PREFERRED EMBODIMENTS

To avoid having to make large incisions from the outside into the body of a patient, particularly when performing abdominal surgery or the like, surgeons often prefer to use laparoscopic techniques. This involves the forming of a relatively small and comparatively easily healed puncture into the patient's abdominal wall, shown in chain lines in FIG. 1 as having a thickness extending between the outer or skin-covered surface 102 and an inside surface 104. It should be understood that the present description is intended to be merely exemplary and not as limiting the potential utility of the claimed invention in any manner.

In practice, into the puncture made into the abdominal wall there is forcibly introduced an elongate, smooth-walled, cylindrical body portion of a cannula 106 formed to a suitable length, preferably in the range 4 in.–10 in., with a diameter in the range ¼ in.–½ in. It may conveniently be made of a strong transparent plastic material such as ABS or Lexan™ by any conventional manufacturing technique. The outer or proximal end of cannula 106 typically has a somewhat enlarged diameter head portion 108 with a flat, circular, end wall 110 provided with a circular aperture (not numbered). Fitted to the rim of this circular aperture is an annular sealing element 112 which has a smooth planar sealing surface 114 and an annular smooth inside sealing surface 116. The enlarged portion 108 of cannula 106 typically is also provided with a planar, smooth-surfaced, pivotally supported sealing flap 118 (shown in a non-sealing position in FIG. 1), which pivots about an internal pivot 120. Sealing flap 118 can thus pivot about pivot 120 so that its smooth planar sealing surface presses evenly across the smooth planar sealing surface 114 of sealing element 112 to, in effect, entirely close off the aperture to seal cannula body 106 to the abdominal cavity. A small biasing spring (not shown) may be provided at pivot 120 to apply a gentle biasing force to sealing flap 118 towards its sealing position in contact with sealing surface 114 as just described.

Typically, more than one such cannula is employed during a surgical procedure. One of these cannulae is fitted to a supply of pressurized gas such as carbon dioxide to insufflate the abdominal cavity in a safe and controllable manner. This permits the surgeon to view various organs inside the abdominal cavity of the patient by light-conveying and/or image-retrieval optic fibers introduced through a neighboring cannula. Once the surgeon has insufflated the abdominal cavity, and has the capability to view and/or project onto an external screen a selected portion of the abdominal cavity and its contents, yet a third cannula is typically introduced so that its internal/distal end is located near the site where surgery is to be performed.

Cannula 106, as described herein, would be the cannula through which one or more surgical tools or instruments may be introduced individually and in succession by a surgeon to perform surgical procedures such as but not limited to incisions, cauterization of incised vessels such as arteries, and coagulation of body fluids which otherwise would tend to interfere with the surgical procedure. However, when such surgical tools are employed, bits of incised/excised body tissues, coagulated fluids, leaked blood, and other surgical debris will tend to adhere to the outside surface of the surgical tool. As the surgeon introduces, uses and then retracts a plurality of surgical tools during an operation it is highly undesirable for the surgical debris to be brought out of the abdominal cavity in an unintended manner and is best avoided to ensure good hygiene and minimal contamination.

As best seen in FIG. 1, according to a preferred embodiment of this invention there is provided an elongate, substantially cylindrical, smooth-walled insertable element with a body 200 which has an external diameter enabling it to be closely but not forcibly slidable into the inside of cannula 106 via the circular sealing element 112. The cylindrical body 200 is also preferably made of a strong, clear, plastics material such as ABS or Lexan™, and is formed to be free of sharp edges.

As best understood with reference to FIG. 2, cylindrical body 200 has an elongate cylindrical wall 202, a distal end 204 thereof, and a proximal end element 208 into which is formed an internal annular recess 206. End element 208 may be made of any suitable material, and has a first end which is shaped and sized to be closely received into recess 206 to be affixed thereto by any known means, e.g., by a suitable adhesive. Element 208 has a second end just inboard of which is provided an annular recess 210 shaped and sized to contain therein an annular sealing element 212 made of a resilient material, e.g., a conventional O-ring. The inner diameter of sealing element 212 is selected to be able to fit sealingly to the outside surface of an elongate surgical tool or instrument 214 in a manner which does not impede translational and/or rotational motion thereof during a surgical operation.

Inboard of and adjacent to distal end 204 of cylindrical body 200, in the first preferred embodiment per FIG. 2, there is provided a plurality of bristle assemblies 300. Each such bristle assembly, e.g., 302 as best seen in the enlarged views per FIGS. 3 and 4, consists of a plurality of soft, flexible, elastic, and initially sterile bristles 304 held by tightly wound coils of a spirally wound central portion 306 of a wire which ends in transversely oriented, straight wire end portions 308, 308.

These straight wire end portions 308, 308 are preferably fitted into small holes (not numbered) drilled through the thickness of cylindrical body 202 to receive them and hold them in place. Since the preferred material for forming cylindrical body 202 is a clear plastics material, it is relatively easy to locate and correctly size these holes to receive the straight wire end portions 308, 308. Likewise, it is easy to use any suitable conventional adhesive and, thereafter, to sterilize the cylindrical body and the groups of bristles held within as described.

Although any number of groups of bristles may thus be provided, three groups appears to be a satisfactory number. The resulting layout is best understood with reference to the enlarged end view per FIG. 5(A) for the first preferred embodiment. As shown there, the three groups of bristles are sized and disposed so that at least some of the bristles, i.e., 310, are disposed with a substantially radially inward orientation relative to the cylindrical body 202. These radially inwardly oriented bristles 310 from each group of bristles 304 tend to be interspersed with each other so as to create a central region filled with bristles. Obviously, a large number of the bristles 304 are oriented either in a substantially circumferential direction or radially outward relative to the cylindrical body 202. All of the bristles cooperate to serve various related and beneficial functions which are described below.

When an elongate surgical tool 214 is pushed past sealing element 212, via proximal end element 208 and through the interior of cylindrical body 202, the distal or working end of the surgical instrument encounters the radially inwardly oriented bristles 310, 310, 310 if the three-group assembly per FIG. 5(A) is utilized. As the elongate body of surgical tool 214 is further advanced past the bristles 310 through cylindrical body 202, and into the abdominal cavity of the patient, the bristles 310 are slightly deformed and maintain a pressing contact with the outer surface of the surgical tool. In other words, by suitable dimensioning, bristles 310 are elastically bent and press radially inward on the outer surface of surgical instrument 214 during its movement and use by the surgeon. Considering that there may be hundreds of such bristles provided, this inherently results in a net radial, inwardly directed, and self-centering biasing force exerted by the bristles to support and position the distal end portion of the surgical instrument centrally within cylindrical body 202.

It should be noted that the resilient, surrounding and sealing force exerted by the resilient annular sealing element 212 also cooperatively provides another supporting and locating force tending to hold the surgical instrument 214 virtually along the axis of cylindrical body 202. In short, sealing element 212 and radially inwardly oriented bristles 310 cooperate to support and centrally located the surgical tool body 214 within the cylindrical body 202 as well as cannula 108. As noted above, sealing element 212 is dimensioned to provide its supporting and sealing function around and relative to the outer cylindrical surface of surgical instrument body 214 without interfering with its motion. The net effect of the radially inwardly oriented bristles 310 does not include a sealing function, and these bristles merely rub against but do not otherwise impede either translational or rotational motion of the surgical instrument body 214 relative to the cannula and/or the patient's abdominal cavity.

It should be appreciated that the surgeon thus always has the freedom to manipulate the cannula, the sealingly contained cylindrical body 202 disposed therein, and the surgical instrument body 214 sealing contained therein. Under these circumstances, pressurized insufflation of the abdominal cavity with a suitable gas, e.g., carbon dioxide, is in no way affected adversely and the cannula and its assorted contents as described above maintain the necessary sealing of the abdominal cavity. The surgeon remains entirely free to manipulate the surgical instrument and to use it as and where necessary within the bounds imposed by the dimensions of the instrument and the presence of organs, etc. within the patient's abdominal cavity.

As described in the earlier-cited U.S. patents, elongate, laser-powered, highly versatile surgical instruments, having generally the same outer surface configuration as for the above-described surgical instrument body 214, are known and utilized by surgeons. Relevant descriptions of the elongate, substantially cylindrical bodies of such surgical instruments are incorporated herein by reference. Such instruments may be laser-powered, apply an electric current to tissue, or perform otherwise, and are selectively used to incise tissue (e.g., cancerous, diseased or damaged tissue, or the like), to cauterize incised vessels (e.g., arteries or veins, assorted ducts from various organs, etc.), to limit the leakage of body fluids therefrom, and to coagulate leaked body fluids, (e.g., blood leakage which may be inevitable). Before long, in such an operational procedure, small but incised bits of tissue, coagulated body fluids, and charred tissue which may be formed during cauterization, begin to appear in the abdominal cavity and some of this surgical debris inevitably adheres to the outside surface of surgical instrument body 214. As the surgeon moves the surgical instrument in and out in translation generally along the axis of the cannula, and rotates the tool to apply power in selected directions, there is bound to be consequential rubbing between the radially inwardly inclined bristles 310 and the outer cylindrical surface of surgical instrument 214. This rubbing serves to scrape off the surgical debris 340 from the outer surface of the surgical instrument body 214. Some of the scraped-off surgical debris will tend to become entangled with and lodged between the radially inwardly oriented bristles 310. Some of the scraped-off surgical debris 350 will also tend to collect just inboard of the distal end 204 of cylindrical body 202 and the rest of bristles 304 which substantially block passage of surgical debris to the inner cylindrical space within cylindrical body 202. The surgical debris is thus continually removed from the outer surface of the surgical instrument 214.

As mentioned earlier, a surgeon may use a particular surgical tool or instrument to perform certain steps in a surgical operation, then use a different tool for a sequential step in the operation, and may even return to a previously-used tool as necessary. By use of the present invention, as described above with particular relevance to the first preferred embodiment, as each such surgical instrument or tool is used and/or withdrawn past the bristles 304 and 310, virtually all of the adhered surgical debris is caught by and/or stuck to these bristles within and inside the distal end portion of cylindrical body 202. Thus, when one tool is so extracted with the scraped-off surgical debris 350 removed therefrom, the insertion of a second surgical tool or instrument past the bristles will, at worst, result only in some of the scraped-off debris 350 being repositioned within the abdominal cavity. However, the newly-inserted surgical tool body, like its predecessor, will also be scraped-clean during its use and, more particularly, when it is withdrawn past the bristles 310 35 and 304.

Given the above-described structure and its mode of use, it becomes clear that a surgeon may employ a surgical tool A, remove it, use a surgical tool B, remove that one, and reintroduce the previously-used surgical tool A without being overly concerned about having left that surgical tool A with surgical debris on or near the patient being operated on. In other words, the present instrument, as described, clearly facilitates maintaining a hygienic and clean environment around the patient's exterior during a surgical operation. It also reduces the risk of body tissue left outside the abdominal cavity being reintroduced after exposure to the operating room atmosphere.

In laparoscopic surgery, as just described, it is quite common to employ another cannula for lavage, i.e., for washing and removal thereby of small bits of surgical debris. Because of the highly-efficient sealing against leakage of insufflation gas, the above-described combination of elements also inherently ensures leakage of the lavage fluid and/or any surgical debris entrained therein. As each surgical tool is withdrawn, for a very short time until another tool is introduced, there is the possibility of a small leakage of insufflation gas occurring past scraped-off surgical debris 350 and all of the bristles 304, 310 into and through the inside space of cylindrical body 202. However, since a fast-working surgeon will undoubtedly pull out one surgical tool and promptly insert another, and because scraped-off surgical debris 350 and the bristles 304, 310 together act to impede such leakage, such leakage should not pose a significant problem.

If the surgeon has to cease surgical operations for any length of time, he or she always has the freedom and option to simply pull out the cylindrical body 200. The moment this is done, under the action of the previously-mentioned biasing spring (not shown), sealing flap 118 will pivot about pivot 120 and should promptly seal against the corresponding sealing surface 114 of annular seal 212, thus ensuring immediate sealing-in of the insufflation atmosphere and/or contents of the abdominal cavity. Then, when the surgeon decides to resume operations, another new, clean and sterile cylindrical body 200 can be pushed past sealing flap 118 and the sealed integrity of the abdominal cavity is ensured immediately upon location of the proximal end element 208 in a sealing relationship with annular seal 112. Because annular sealing element 112 is formed of a resilient material, e.g., a chemically-inert silicone material, a forcible but disengageable engagement between annular sealing element 112 and proximal end element 208 can be made easily and effectively by appropriate choice of dimensions. In other words, cylindrical body 200 will not be dislodged inadvertently.

In a second preferred embodiment, as illustrated in FIGS. 6–9, a plurality of bristles 610, every one of which is oriented substantially radially inward of cylindrical body 202, is provided inboard of the distal end 204. As best seen with reference to FIG. 7, these bristles 610 are sized so that they preferably end just short of the central axis of cylindrical body 202 yet, as best seen in FIG. 8, when an elongate body 214 of a surgical instrument is disposed within the distal ends of bristles 610 they are forcibly pressed thereagainst. Thus, in this embodiment, by suitable sizing and selection of the materials of bristles 610 it is possible to ensure the desired efficient central supporting and scraping contact by the bristles 610 on the outer surface of elongate surgical instrument 214.

As a practical matter, a flexible sheet 900, formed of a flexible sterilizable material, is provided with a plurality of preferably evenly distributed bristles 610 of suitable size. The flat element 900 is formed or cut to have a length "L" preferably in the range 0.5–1.5 in., and a width corresponding closely to the inside circumference of cylindrical body 202. Thus, when flexible element 900 is rolled up into the form of a cylinder, pushed into the distal end of cylindrical body 202, and adhered therein, the net result is that the bristles 610 are all radially inwardly disposed and held in place as desired. As seen in FIG. 9, by proper dimensioning of base element 900, there should be at most only a very small circumferential gap 902 where the adjacent edges of rolled-up element 900 are disposed in their final position.

As best seen in FIGS. 4 and 8, the external cylindrical surface of elongate surgical tool body 214 has a diameter "d". In the first preferred embodiment, as best seen in FIG. 5(A), radially inwardly oriented bristles 310 of the different groups of bristles may be interspersed with each other. The reason for making this arrangement is to ensure that the relatively few bristles that are so inclined can cooperate effectively in scraping the surgical debris off the outer surface of the surgical tool inserted therethrough. In the second preferred embodiment per FIGS. 6–9, however, since all the bristles 610 are deliberately made to be radially inwardly oriented, it should be sufficient if their distal ends define an empty cylindrical space of diameter "$d_o$" such that $d > d_o$. See FIG. 8. The difference just defined can be selected in light of the thickness and lengths of the bristles 610 and the material of which they are made. The inside diameter of cylindrical body 202 is shown in FIGS. 6–9 as "D" and should be virtually the same as the rolled-up diameter of the base element 900.

The bristles may be made of a material such as nylon, but may also be made of any other suitable elastic but firm and readily sterilizable plastics material. The entire assembly of the cylindrical body 200, with its proximal end element 208, circular sealing element 212, and the bristles and/or bristles-supporting wires, etc., need not be prohibitably expensive since they are all made of conventionally available materials and are required to be present only in small quantities. Extreme precision of dimensions is not required, although smooth external surface finishes are needed to ensure proper sealing. The entire cylindrical body assembly is, therefore, an element which is disposable. In fact, because the surgical debris is left entangled with the bristles, sterilization for subsequent reuse of the cylindrical body 200 is not contemplated. The cannula body 100, however, may be sterilized after the annular seal 112 thereof is removed. The discarded seal is then replaced with a new sterile seal. The surgical instrument may or may not be disposable, depending on its design, cost and nature of use.

The invention, in the various embodiments as described above, permits use of a relatively inexpensive and disposable element which, by appropriate sizing, can be used with a wide variety of surgical instruments and conventional cannulae to provide a much desired benefit, i.e., the routine and prompt removal of surgical debris from a succession of surgical tools or instruments used in complex surgical operations.

Although the present invention has been described and illustrated in detail, it should be clearly understood that the same is by way of example only and is not to be taken by way of limitation, the spirit and scope of the present invention being limited only by the terms of the appended claims.

What is claimed is:

1. Apparatus for supporting and cleaning an elongate surgical instrument during use thereof within a cylindrical cannula, comprising:

a cylindrical body shaped and sized to sealingly fit closely inside the cannula along a longitudinal axis thereof;

a plurality of bristles mounted inside a distal end of the cylindrical body, at least a portion of the bristles being disposed to be directed generally radially inward of the cylindrical body; and a cylindrical inlet element fitted to a proximal end of the cylindrical body, comprising a sealing element for supporting a proximal end of an elongate surgical instrument and resiliently sealing around an outer surface of the elongate surgical instrument inserted therethrough, said portion of the bristles being sized to contact an outer surface of a distal end of the surgical instrument.

2. Apparatus for supporting and cleaning an elongate surgical instrument during use thereof within a cylindrical cannula, comprising:

a cylindrical body shaped and sized to sealingly fit closely inside the cannula along a longitudinal axis thereof;

a plurality of bristles mounted inside a distal end of the cylindrical body, at least a portion of the bristles being disposed to be directed generally radially inward of the cylindrical body; and a cylindrical inlet element fitted to a proximal end of the cylindrical body, comprising a sealing element for supporting a proximal end of an elongate surgical instrument and resiliently sealing around an outer surface of the elongate surgical instrument inserted therethrough, said portion of the bristles being sized to contact an outer surface of a distal end of the surgical instrument, wherein the bristles are each mounted at a respective first end to an element which is sized and shaped to be rolled into a cylindrical form which is then fitted into and attached to an inside cylindrical surface at a distal end of the cylindrical body so that the bristles are all disposed to be oriented substantially radially inward of the cylindrical body, and the bristles are dimensioned so that they are forcibly deformed by and press with their distal ends against an outer surface of the surgical instrument inserted into the cylindrical body.

3. The apparatus according to claim 2, wherein:

the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

4. Apparatus for supporting and cleaning an elongate surgical instrument during use thereof within a cylindrical cannula, comprising:

a cylindrical body shaded and sized to sealingly fit closely inside the cannula along a longitudinal axis thereof;

a plurality of bristles mounted inside a distal end of the cylindrical body, at least a portion of the bristles being disposed to be directed generally radially inward of the cylindrical body; and a cylindrical inlet element fitted to a proximal end of the cylindrical body, comprising a sealing element for supporting a proximal end of an elongate surgical instrument and resiliently sealing around an outer surface of the elongate surgical instrument inserted therethrough, said portion of the bristles being sized to contact an outer surface of a distal end of the surgical instrument, wherein the plurality of bristles is divided into groups of bristles, each individual group of bristles being held in a central spirally-wound portion of a wire which is provided with two transverse mounting portions at opposite ends, whereby the spirally-wound central portions of the wires are positioned inside the cylindrical body with the corresponding straight transverse portions mounted to the cylindrical body.

5. The apparatus according to claim 4, wherein:

the plurality of bristles is divided into three groups of bristles which are disposed evenly around an axis of the cylindrical body, so that bristles of said portions of the groups of bristles which are disposed to be directed generally radially inward are sized to ensure forcible deformation when the body of a surgical instrument is located within the cylindrical body, whereby the deformed bristles press radially inward against an outer surface of the surgical instrument so as to support the same substantially axially of the cylindrical body and so as to rub against said outer surface of the surgical instrument whenever the surgical instrument is moved either axially or rotationally relative to the cylindrical body.

6. The apparatus according to claim 5, wherein:

the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

7. The apparatus according to claim 4, wherein:

the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

8. Apparatus for supporting and cleaning an elongate surgical instrument during use thereof within a cylindrical cannula, comprising:

a cylindrical body shaped and sized to sealingly fit closely inside the cannula along a longitudinal axis thereof;

a plurality of bristles mounted inside a distal end of the cylindrical body, at least a portion of the bristles being disposed to be directed generally radially inward of the cylindrical body; and a cylindrical inlet element fitted to a proximal end of the cylindrical body, comprising a sealing element for supporting a proximal end of an elongate surgical instrument and resiliently sealing around an outer surface of the elongate surgical instrument inserted therethrough, said portion of the bristles being sized to contact an outer surface of a distal end of the surgical instrument, wherein the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

9. A method of supporting and cleaning an elongate surgical instrument during use thereof within a cylindrical cannula, comprising the steps of:

sealingly and closely fitting into and along a longitudinal axis of the cannula a correspondingly shaped and sized cylindrical body;

inside a distal end of the cylindrical body providing a plurality of bristles, at least a portion of the bristles being disposed to be directed generally radially inward of the cylindrical body; and providing a sealing element at a proximal end of the cylindrical body, the sealing element being shaped, sized, and disposed to resiliently fit sealingly around an outer surface of an elongate surgical instrument inserted therethrough when a distal end portion of the surgical instrument is disposed so as to be contacted by the generally radially inwardly disposed portion of the bristles, whereby the sealing element and the bristles cooperatively contact the outer surface of the surgical instrument and support the same, and relative contacting movement between the surgical instrument and the contacting fibers results in scraping off of any surgical debris adhered to the outside surface of the surgical instrument.

10. The method according to claim 9, wherein:
the bristles are provided in a plurality of groups of bristles, wherein each individual group of bristles is gripped by a coiled central portion of a wire which has opposite ends supported to and inside a distal end of the cylindrical body.

11. The method according to claim 9, wherein:
said bristles are initially mounted at respective base ends to an element which is then rolled to a cylindrical shape and fitted to an inside surface of the cylindrical body adjacent a distal end thereof.

12. A system for enabling laparoscopic surgery via a single cannula, in a manner which allows a surgeon to operate with a succession of elongate surgical tools each extractable after a use substantially free of incised tissue and incidental surgical debris, comprising:

a cylindrical cannula having an open distal end and a closeable end, wherein the closeable end has a pivotably mounted sealing flap and an aperture provided with a resilient annular peripheral seal having a first sealing portion sealable by the sealing flap and a circular second sealing portion sized and shaped to surround and seal to a cylindrical surface;

a cylindrical body shaped and sized to fit closely inside the cannula along a longitudinal axis thereof, wherein the cylindrical body has a cylindrical inlet element fitted to a proximal end, the cylindrical inlet element having both an outer cylindrical surface shaped and sized to sealingly fit to the second circular portion of the peripheral seal and a sealing element for resiliently sealing around a proximal end portion of an outer surface of an elongate surgical instrument inserted therethrough; and a plurality of bristles mounted inside a distal end of the cylindrical body with at least a portion of the bristles being disposed to be directed generally radially inward of the cylindrical body, wherein said portion of the bristles is sized to contact a distal end portion of said outer surface of the surgical instrument.

13. The system according to claim 12, wherein:
the plurality of bristles is divided into groups of bristles, each individual group of bristles being held in a central spirally-wound portion of a wire which is provided with two transverse mounting portions at opposite ends, whereby the spirally-wound central portions of the wires are positioned inside the cylindrical body with the corresponding transverse portions mounted to the cylindrical body.

14. The system according to claim 13, wherein:
the plurality of bristles is divided into three groups of bristles which are disposed evenly around an axis of the cylindrical body, so that bristles of said portions of the groups of bristles which are disposed to be directed generally radially inward are sized to be forcibly deformed when the body of a surgical instrument is inserted within the cylindrical body, whereby the deformed bristles press radially inward against an outer surface of the surgical instrument so as to support the same substantially axially of the cylindrical body and so as to rub against said outer surface whenever the surgical instrument is moved either axially or rotationally relative to the deformed bristles.

15. The system according to claim 14, wherein:
the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

16. The system according to claim 13, wherein:
the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

17. The system according to claim 12, wherein:

the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

18. The system according to claim 12, wherein:

the bristles are each mounted at a respective first end to an element which is sized and shaped to be rolled into a cylindrical form which is then fitted into and attached to an inside cylindrical surface at a distal end of the cylindrical body so that the bristles are all disposed to be oriented substantially radially inward of the cylindrical body, and the bristles are dimensioned so that they are forcibly deformed by and press with their distal ends against an outer surface of the surgical instrument inserted into the cylindrical body.

19. The apparatus according to claim 18, wherein:

the cylindrical inlet element is permanently affixed to the proximal end of the cylindrical body at a first end and has a circular annular central recess inside of and adjacent to a second end, said recess being shaped and sized to hold said sealing element in such a manner that when the elongate surgical instrument is inserted through the cylindrical inlet element the sealing element elastically presses around, supports, and seals to an outside surface of the surgical instrument yet permits both relative translational and rotational motion thereof.

* * * * *